United States Patent
Shima et al.

(10) Patent No.: US 8,008,515 B2
(45) Date of Patent: Aug. 30, 2011

(54) CATALYST FOR PARTIAL OXIDATION OF OLEFIN, PREPARATION METHOD THEREOF, AND PROCESS FOR PREPARING ALKYLENE OXIDE

(75) Inventors: Masahide Shima, Kobe (JP); Masafumi Sugio, Himeji (JP); Tatsuya Kawabata, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 12/298,978

(22) PCT Filed: May 1, 2007

(86) PCT No.: PCT/JP2007/059335
§ 371 (c)(1),
(2), (4) Date: Feb. 25, 2009

(87) PCT Pub. No.: WO2007/129649
PCT Pub. Date: Nov. 15, 2007

(65) Prior Publication Data
US 2009/0299104 A1    Dec. 3, 2009

(30) Foreign Application Priority Data

May 2, 2006  (JP) .................................. 2006-128104

(51) Int. Cl.
*C07D 301/10*  (2006.01)
*B01J 21/12*  (2006.01)

(52) U.S. Cl. ..................... 549/534; 502/243; 502/348

(58) Field of Classification Search ................... 502/243, 502/348; 549/534
See application file for complete search history.

(56) References Cited

U.S. PATENT DOCUMENTS

| | | |
|---|---|---|
| 4,033,903 A | 7/1977 | Maxwell |
| 5,077,256 A | 12/1991 | Yamamoto et al. |
| 5,395,812 A | 3/1995 | Nagase et al. |
| 6,103,916 A * | 8/2000 | Takada et al. .......... 549/534 |
| 6,153,556 A * | 11/2000 | Shima et al. .......... 502/348 |
| 6,787,656 B2 * | 9/2004 | Shima et al. .......... 549/534 |

FOREIGN PATENT DOCUMENTS

| | | |
|---|---|---|
| EP | 0 380 295 A2 | 8/1990 |
| EP | 1 086 743 A1 | 3/2001 |
| EP | 1 308 442 A1 | 5/2003 |
| JP | 55-145677 A | 11/1980 |
| JP | 2-194839 A | 8/1990 |
| JP | 5-329368 A | 12/1993 |
| JP | 10-503709 A | 4/1998 |
| WO | WO 96/04989 A1 | 2/1996 |
| WO | WO 2005/023418 A1 | 3/2005 |

OTHER PUBLICATIONS

International Preliminary Report on Patentability and Written Opinion (Forms PCT/IB/326, PCT/IB/373 and PCT/ISA/237) issued in PCT/JP2007/059335, Nov. 14, 2008, and English-language translation thereof (Forms PCT/IB/338, PCT/IB/373 and PCT/ISA/237).
Form PCT/ISA/210 (International Search Report) dated Jul. 3, 2007.
Form PCT/ISA/237 (Written Opinion of the International Searching Authority) dated Jul. 3, 2007.
Extended Search Report from European Patent Office issued in corresponding European Patent Application No. 07742770.6 dated May 20, 2011.

* cited by examiner

*Primary Examiner* — Sikarl Witherspoon
(74) *Attorney, Agent, or Firm* — Buchanan, Ingersoll and Rooney PC

(57) ABSTRACT

A catalyst for partial oxidation of olefin, which comprises silver or silver oxide and an alkali metal or a compound thereof supported on an α-alumina carrier containing silicon or a compound thereof, wherein the silicon or the compound thereof exists at a position substantially identical to that of a particle of the alkali metal or the compound thereof, a preparation method thereof, and a process for preparing olefin oxide which comprises subjecting olefin to vapor-phase oxidation with a molecular oxygen-containing gas in the presence of the catalyst.

26 Claims, 4 Drawing Sheets

US 8,008,515 B2

CATALYST FOR PARTIAL OXIDATION OF OLEFIN, PREPARATION METHOD THEREOF, AND PROCESS FOR PREPARING ALKYLENE OXIDE

TECHNICAL FIELD

The present invention relates to a catalyst for partial oxidation of olefin, and a preparation method thereof, and a process for preparing olefin oxide by vapor-phase oxidization of olefin with molecular oxygen-containing gas in the presence of the catalyst.

BACKGROUND ART

In the past, a lot of literatures have been introduced about a catalyst for producing ethylene oxide by vapor-phase oxidation of ethylene with molecular oxygen-containing gas, and a carrier thereof. For example, JP-A-55-145,677 discloses a production method of ethylene oxide consists of using a silver catalyst, in which silver and, if needed, further alkali metal component or alkaline earth metal component are supported on a nonacidic carrier, wherein total content of alumina, silica and titania is 99% by weight or more, and the metal content of each group of Va, VIa, VIII, Ib and IIb of the periodic table is less than 0.1% by weight as total amount of a metal oxides, and which does not show an acid color by the methyl red as indicator of pKa +4.8. In addition, there is proposed a catalyst for producing ethylene oxide (U.S. Pat. Nos. 5,077,256 and 5,395,812), in which silver and cesium are supported as catalyst components onto an α-alumina carrier wherein covering layer of amorphous silica is provided on the surface of the carrier.

DISCLOSURE OF THE INVENTION

A catalyst according to the above U.S. Pat. Nos. 5,077,256 and 5,395,812 is satisfiable with catalyst performance on some level. However, since production size of ethylene oxide is enormous, even only 1% improvement of selectivity can remarkably save ethylene of raw material, therefore, a catalyst for producing ethylene oxide which has more excellent catalyst performance, a preparation method thereof, and a process for preparing ethylene oxide using this catalyst are desired.

The above purposes are attained by the following (1)-(11).

(1) A catalyst for partial oxidation of olefin, which comprises silver or silver oxide and an alkali metal or a compound thereof supported on an α-alumina carrier containing silicon or a compound thereof, wherein the silicon or the compound thereof exists at a position substantially identical to that of a particle of the alkali metal or the compound thereof.

(2) The catalyst according to (1) above, wherein a silver particle exists at a different position from that of (a) the silicon or the compound thereof and/or (b) the particle of the alkali metal or the compound thereof.

(3) The catalyst according to (1) or (2) above, wherein content of (a) the silicon or the compound thereof converted to as $SiO_2$ is 0.01 to 6% by mass relative to total amount of the carrier, and supported amount of (b) the alkali metal or the compound thereof (converted to as $M_2O$, wherein M is an alkali metal) and supported amount of (c) the silver are 0.01 to 5% by mass and 1 to 45% by mass, respectively, relative to α-alumina.

(4) The catalyst according to any one of (1) to (3) above, wherein content of (a) the silicon or the compound thereof converted to as $SiO_2$ is 0.1 to 5% by mass relative to α-alumina, and supported amount of (b) the alkali metal or the compound thereof (converted to as $M_2O$, wherein M is an alkali metal) and supported amount of (c) the silver are 0.1 to 1% by mass and 5 to 20% by mass, respectively, relative to α-alumina.

(5) The catalyst according to any one of (1) to (4) above, wherein content of α-alumina in the carrier is 89 to 99.9% by mass.

(6) The catalyst according to any one of (1) to (5) above, wherein the alkali metal is cesium.

(7) A preparation method of a catalyst for partial oxidation of olefin which comprises impregnating an α-alumina carrier containing silicon or a compound thereof with an aqueous solution containing a silver compound and an alkali metal compound, drying the impregnated carrier, calcining the carrier in an oxidizing atmosphere at a temperature of 150 to 250° C. for 0.1 to 10 hours, further calcining the carrier in an oxidizing atmosphere at a temperature of 250 to 450° C. for 0.1 to 10 hours, and heat-treating the carrier in an inert gas atmosphere at a temperature of 450 to 700° C. for 0.1 to 10 hours.

(8) The method according to (7) above, wherein -alumina content in the carrier is 89 to 99.9% by mass and content of the silicon or the compound thereof, converted to as $SiO_2$, is 0.01 to 6% by mass.

(9) A process for preparing olefin oxide which comprises subjecting olefin to vapor-phase oxidization with a molecular oxygen-containing gas in the presence of the catalyst set forth in any one of (1) to (6) above.

(10) The method according to (10) above, wherein the olefin is ethylene.

BEST MODE FOR CARRYING OUT THE INVENTION

Figure 1:
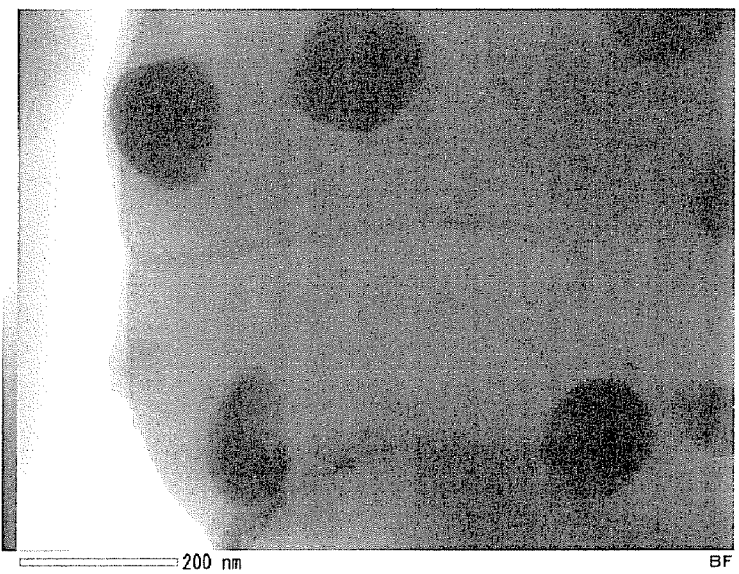
FIG. 1 is a photograph in which silver, silicon and cesium are measured by FE-TEM and EDS for an identical part of the catalyst of Example 1, showing distribution of the silver on the catalyst surface, wherein white parts indicate silver.

The catalyst according to the present invention is, as described above, the catalyst for partial oxidation of olefin, wherein a silver or a silver oxide and an alkali metal or a compound thereof are supported on α-alumina carrier containing a silicon or a compound thereof, and an existing position of said silicon or compound thereof and an existing position of a particle of the alkali metal or compound thereof is almost the same.

<Carrier>

The carrier according to the present invention is an α-alumina carrier which essentially contain silicon. It can be suitably used an ingredient usually used for catalyst carrier, for example, aluminum, an alkali metal, an alkaline earth metal, etc. Usually, these elements exist in the state of an oxide, a composite oxide, etc.

The aluminum in the carrier exists in a form of α-alumina, β-alumina, γ-alumina, silica alumina, etc., and among them, α-alumina is suitable. However, an aluminum compound other than α-alumina may be added. There is no particular restriction of α-alumina itself, and any type of α-alumina can be used as long as it is generally used as α-alumina. As to the α-alumina, although it can be obtained by heat-treating α-alumina precursors such as aluminum hydroxide, β-alumina and γ-alumina, in particular, α-alumina obtained by Bayer process calcination is used suitably, and $Al_2O_3$ content is suitably 89% by mass or more, preferably 97% by mass or more, and more preferably 99% by mass or more.

As the silicon or the silicon compound according to the carrier used in the present invention, any type can be used as long as silicon itself or other silicon compound is included, for example, a compound which can form an amorphous layer of silica-calcium-potassium-iron by calcining silicon with a calcium compound, a potassium compound, an iron compound, etc. can be used. A typical example thereof includes silica, feldspar, clay, silicon nitride, silicon carbide, silane, and a silicate.

In addition, an alumino-silicate such as silica-alumina, mullite can be included. They may be used singly or in combination with two or more members. In addition, they can be synthetic products or natural products. There is no particular restriction of forms of the silicon compounds, and they may be added by any forms such as powder, sol and solution, etc.

When these silicon or silicon compound is powder, one having an average particle size of 1 to 300 nm, preferably 1 to 20 nm is used suitably. Among these silicon or silicon compounds, colloidal silica having an average particle size of 1 to 300 nm, preferably 1 to 20 nm is suitably used. This colloid-type silica is preferably used as an aqueous solution from the ease of dispersions. The colloidal silica can be obtained by a peptisation method comprising neutralizing a solution of sodium silicate with an acid to make a gel once, and then deflocculating the gel, or by an ion exchange method comprising removing sodium from the solution of sodium silicate, for example.

Content of the silicon is 0.01 to 6% by mass, preferably 0.1 to 5% by mass, and more preferably 0.2 to 3% by mass, converted to as $SiO_2$, relative to total amount of the carrier. That is, when the content of the silicon is less than the above range or exceeds the above range, selectivity to ethylene oxide and/or catalytic activity is lowered, therefore it is not desirable.

Content of the alkali metal in the carrier used in the present invention is 0.01 to 5% by mass, preferably 0.05 to 3% by mass, and more preferably 0.1 to 1% by mass, converted to as a stable oxide, relative to the total amount of the carrier. That is, when the content of the alkali metal is less than the above lower limit or exceeds the above upper limit, the selectivity to ethylene oxide is lowered, therefore it is not desirable.

Preparation method of the carrier to be used for the catalyst of the present invention, for example, is carried out by; adding a silicon compound, a calcium compound, a potassium compound, an iron compound and an organic binder to powdered α-alumina or powdered α-alumina precursor in water or an aqueous solution to obtain a sludge; molding the sludge to forming a molded component; drying the molded component; and then calcining the dried component at a temperature of 1000 to 2000° C.

That is, specifically, for example, a predetermined quantity of the silicon compound, and if needed, a calcium compound, a potassium compound and an iron compound and an organic binder are added to powdered α-alumina, and further, water is added if needed, and mixed enough with using a kneading machine such as kneader, and then granulated by extrusion molding method or other method, and dried at a temperature of 80 to 900° C., preferably 90 to 200° C., for 0.01 to 100 hours, more preferably for 0.1 to 30 hours, and subsequently calcined at a temperature of 1000 to 2000° C., preferably 1200 to 1700° C., more preferably 1300 to 1700° C. in an oxidizing atmosphere, for 0.1 to 100 hours, preferably 1 to 30 hours. Subsequently, the product is cooled with the cooling rates of 0.1 to 100° C./min, preferably 10 to 90° C./min under an air and/or $N_2$ atmosphere, and after cooling to 900° C., it cools down to room temperature. It should be noted that the drying may be omitted in some cases.

The carrier, which was thus subjected to calcining and cooling to room temperature, is subjected to washing. As for the washing, boiling washing by deionized water is preferable and it is suitable to wash so that the specific resistance of the cleaning liquid after washing is 10,000 Ωcm (25° C.) or more, preferably 5,000 to 1,000,000 Ωcm (25° C.), however, washing may be omitted in some cases.

As the organic binder, carboxy methylcellulose, methylcellulose, hydroxyethyl cellulose, Gum arabic, polyvinyl alcohol and cornstarch are included, and the organic binder is used in a content of 0.1 to 100% by mass, preferably 1 to 50% by mass, relative to the material forming the carrier. In addition, the material adjusted a hull such as peach, apricot, walnut and a seed etc. to uniform particle size, or the substance which has a uniform particle diameter and evanishes by calcining, may be used as a pore forming agent together with the organic binder.

As the powdered α-alumina or α-alumina precursor, one having a particle size of 0.1 to 200 μm, preferably 1 to 100 μm is used.

There is no special limitation in form of the carrier of the catalyst of the present invention, and usually it is used in a granular form such as spherical form, pellet form, and ring form. In addition, as for the size, the mean equivalent diameter of the carrier is usually 3 to 20 mm, preferably 5 to 10 mm.

The BET (Brunaer-Emett-Teller) specific surface area of the carrier is 0.03 to 10 m²/g, preferably 0.1 to 5 m²/g, and more preferably 0.3 to 2 m²/g. That is, when the specific surface area is less than the above lower limit, the sufficient water absorption rate can not be obtained, on the other hand, when the specific surface area exceeds the above upper limit, the pore size becomes small and sequential oxidization of ethylene oxide, the reaction product produced by use of the catalyst using the carrier, is accelerated, therefore it is not desirable.

The water absorption rate of the carrier is usually 10 to 70%, preferably 20 to 60% and more preferably 30 to 50%. That is, when the water absorption rate is less than the above lower limit, supporting of a catalyst component becomes difficult due to the low water absorption rate, and adversely when the water absorption rate exceeds the above upper limit, sufficient crushing strength will be hard to be obtained.

The mean pore size of the carrier is usually 0.1 to 5 μm, preferably 0.2 to 3 μm, more preferably 0.3 to 0.9 μm. That is, when the mean pore size exceeds the above upper limit, the activity of the catalyst produced using the carrier is lowered, on the other hand, when it is less than the above lower limit, the serial oxidation reaction of the ethylene oxide, which is the product, is promoted due to gas retention. In addition, porosity of the carrier is usually 40 to 80%, preferably 50 to 70%. When the porosity is less than the above lower limit, specific gravity of the carrier becomes large too much, on the other hand, when the porosity exceeds the above upper limits, sufficient crushing strength of the carrier is hard to be obtained.

<Catalyst Preparation>

The catalyst for partial oxidation of olefin according to the present invention can be prepared by subjecting silver and an alkali metal or an alkali metal compound to be supported by the carrier. The catalyst component supported by the carrier is silver, and an alkali metal or an alkali metal compound as reaction accelerator.

Preferably, this method comprises, for example, preparing an aqueous solution only containing a silver compound for forming silver or that containing a silver compound, a complex agent for making a silver complex, and an alkali metal compound as a reaction promoter; impregnating a carrier with the solution; drying the impregnated carrier; and calcining the carrier. This drying is preferably carried out in an oxidizing gas such as air and oxygen gas, or an inert gas atmosphere such as nitrogen, preferably in an air atmosphere at a temperature of 80 to 100° C.

It is preferable to carry out calcination in an oxidizing gas such as air and oxygen gas, or an inert gas atmosphere such as nitrogen at a temperature of 150 to 700° C. It should be noted that, this calcination may be carried out in one step or two steps or more. Especially, it is suitable that the first step is carried out in an oxidizing atmosphere at a temperature of 150 to 350° C., preferably 180 to 250° C. for 0.01 to 10 hours, preferably 0.1 to 5 hours, and the second step is carried out in an oxidizing atmosphere containing oxygen gas at a temperature of 250 to 500° C., preferably 280 to 450° C. for 0.01 to 10 hours, preferably 0.1 to 5 hours. Furthermore, it is preferable that the third step is carried out in an atmosphere of at least one inert gas selected from the group consisting of nitrogen, helium and argon, or in a reducing gas atmosphere such as hydrogen and carbon monoxide, or in a mixture atmosphere of the inert gas and the reducing gas, preferably in the inert gas atmosphere, at a temperature of 450 to 700° C., preferably 500 to 650° C. for 0.1 to 10 hours, preferably 0.5 to 8 hours.

As a typical example of the above silver compound, silver nitrate, silver carbonate, silver oxalate, silver acetate, silver propionate, silver lactate, silver citrate, silver neodecanoate etc. can be included. As a typical example of the complexing agent, monoethanolamine, diethanolamine, triethanolamine, ethylenediamine, propylenediamine etc. can be included. A typical example of the reaction accelerator is alkali metal such as lithium, sodium, potassium, rubidium and cesium, and preferably cesium. In addition, thallium, sulfur, chromium, molybdenum, tungsten etc. can be used together if needed. These can be used singly or in combination of two or more members.

Carrier amount of silver is 1 to 45% by mass, preferably 5 to 25% by mass, converted to as metallic silver, relative to the carrier. In addition, carrier amount of the alkali metal to be supported at catalyst preparation is 0.0001 to 3% by mass, preferably 0.001 to 2% by mass, more preferably 0.01 to 1% by mass, converted to as $M_2O$ (wherein M is an alkali metal), relative to the carrier.

As the alkali metal, lithium, sodium, potassium, cesium, rubidium and the like are included. Cesium is preferable.

In the catalyst of the present invention thus obtained, a particle of silicon or a compound thereof, for example, silicon oxide such as $SiO_2$, which exists in fine pores or on the surface of other parts of the α-alumina carrier containing silicon or a compound thereof, does not always exist in uniform distribution but exists unevenly distributed in a certain region, and a particle of an alkali metal oxide [$M_2O$ (wherein M is an alkali metal)], for example, $Cs_2O$ exists at the vicinity of the existing position of the particle of silicon or a compound thereof.

On the other hand, a particle of silver or oxide thereof does not exist in the site where the particle of the silicon compound and the particle of the alkali metal compound mainly exist, but mainly exists in the other regions, and the mean diameter thereof is 10 to 500 nm, preferably 30 to 300 nm.

These phenomena become apparent by measuring silver, alkali metal and silicon by FE/TEM and XAFS on the same point of catalysts obtained by the present invention, and investigating distribution of each component. As the result, from the resulting photograph, distribution of the particle of the silver or the oxide thereof (FIG. 1), distribution of the silicon or the compound thereof (FIG. 2), and distribution of alkali metal or oxide thereof (FIG. 3), become clear, showing that the silicon and the alkali metal exist at substantially identical position. In addition, a localization frequency of the alkali metal or the compound thereof relative to the silicon or the compound thereof is 60 to 99.9%, preferably 80 to 99%. It should be noted that, here, the localization frequency can be expressed with [((area in which Si and Cs overlap per unit area)/(area of Si per unit area)) ×100] in the EDS image of FE-TEM.

On the contrary, it turns out that the silver exists in a different region from that the silicon and the alkali metal exist.

Figure 4:
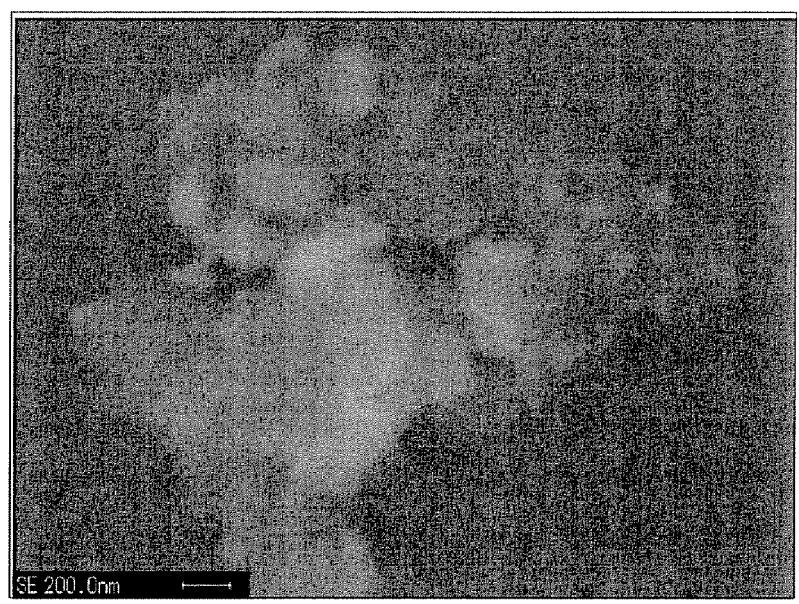
FIG. 4 is a photograph in which the catalyst of Comparative Example 1 is measured in a manner similar to Example 1, showing distribution of the silver on the catalyst surface, wherein white parts indicate silver.
Figure 5:
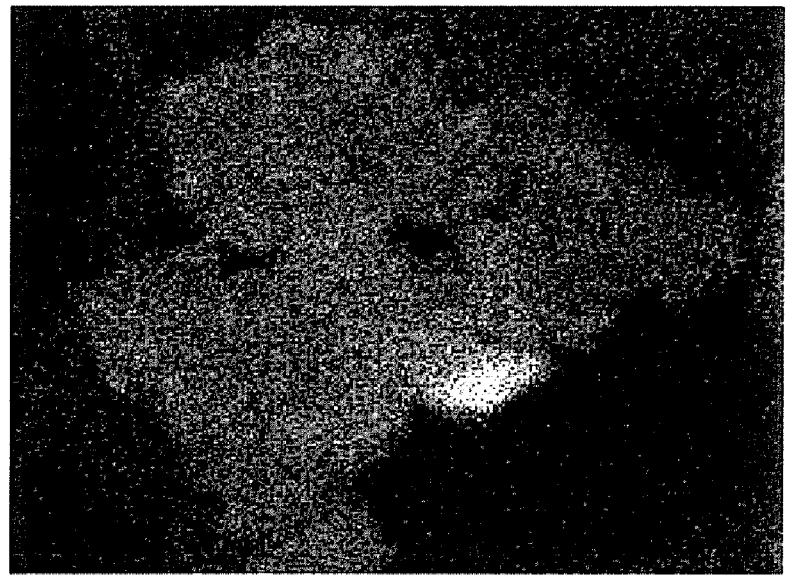
FIG. 5 is a photograph in which the catalyst of Comparative Example 1 is measured in a manner similar to Example 1, showing distribution of the silicon on the catalyst surface, wherein white parts indicate silicon.
Figure 6:
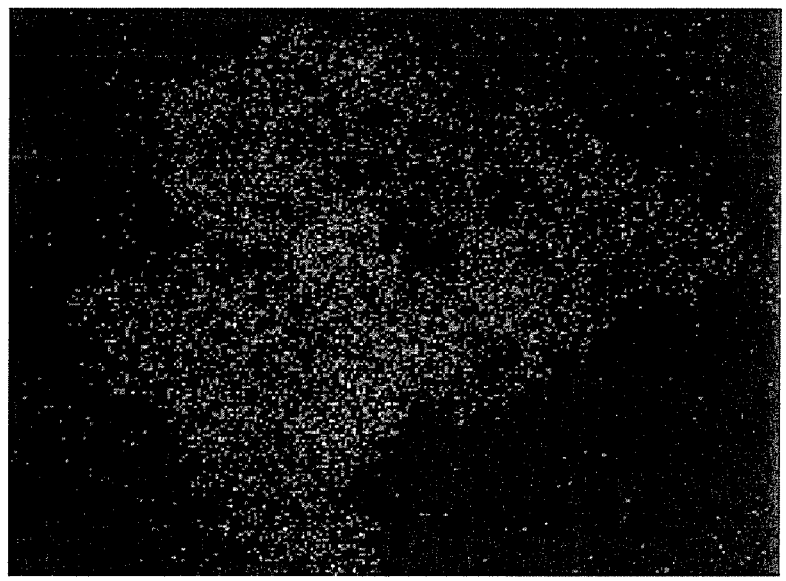
FIG. 6 is a photograph in which the catalyst of Comparative Example 1 is measured in a manner similar to Example 1, showing distribution of the cesium on the catalyst surface, wherein white parts indicate cesium.

On the other hand, in a conventional catalyst, as shown in FIG. 4 (silver particle), FIG. 5 (silicon compound particle) and FIG. 6 (alkali metal oxide particle), particle size of the silver or the silver oxide particle is large and is not independent, in addition, the particle of the silicon or the silicon compound (for example, silica) is not unevenly distributed, and the existing position of the particle of the alkali metal oxide is not identical to that of the silicon compound.

In addition, two samples; sample A (a catalyst of an α-alumina-$SiO_2$ carrier (containing 2% by mass of $SiO_2$) supporting $Ag_2O$ of 1% by mass) and sample B (a catalyst of an α-alumina-$SiO_2$ carrier (containing 2% by mass of $SiO_2$) supporting $Ag_2O$ of 1% by mass and Cs of 0.1% by mass) prepared by similar manner to the following Example 1 except for composition); were ground in an agate mortar. Then the ground samples were press molded, and sealed in a polyethylene film having a thickness of 80 μm, to prepare the catalyst. Ag, $Ag_2O$ and AgO were similarly prepared for reference.

These were measured by the transmission methods with the ion chamber detector, with using Si (111) monochromator in the BL19 B-2 line of Spring-8.

Figure 7:
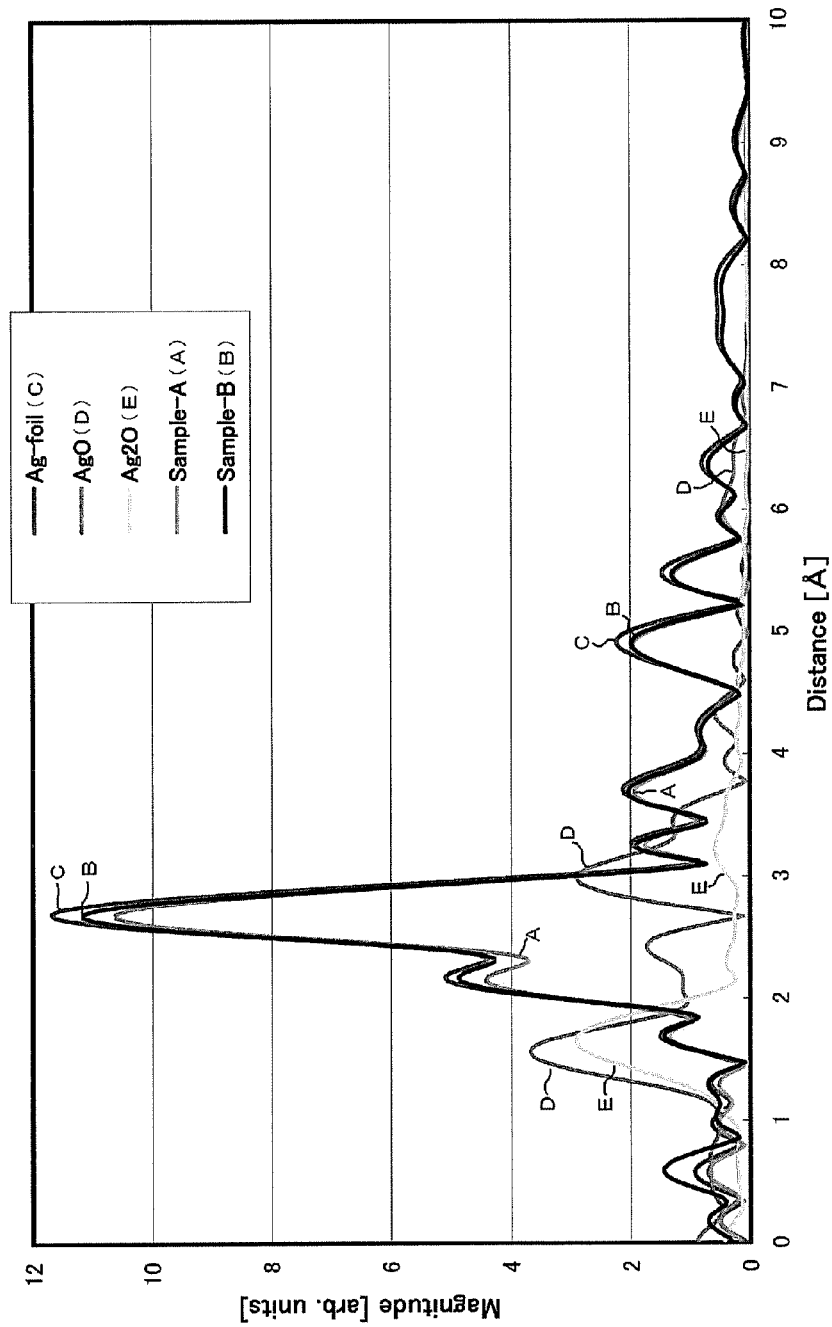
FIG. 7 is a graph showing the relation of distance between a catalyst of α-alumina carrier and a reference sample and absorption intensity, obtained as a result of the Fourier transformation of EXAFS.

In addition, as shown in FIG. 7, both sample A and B showed the similar peak form to reference Ag, from the result of the Fourier transform of EXAFS (extended x-ray absorption fine structure). The trace of other elements was not observed in the circumference of Ag in the catalyst. It should be noted that, in this figure, curve A is derived from sample A, curve B is derived from sample B, curve C is derived from Ag foil, curve D is derived from AgO, and curve E is derived from $Ag_2O$.

The information obtainable from EXAFS is described in 42 to 48 page of "Actual conditions of solid surface characterization" (Feb. 10, 2005/published from Kodansha Ltd.) edited by Yasuhiro Tanaka and Hiromi Yamashita. The vibrational structure observed in a range from an absorption edge to 1000 eV is the structure called EXAFS. This vibrational structure fundamentally arises from an electronic transition of the same character as the complicated band just behind the absorption edge. However, since it is away from the absorption edge, the energy of the free electron emitted by excitation is high, the probability of front scattering passing a neighboring atom and the probability of back scattering repelled to 180 degree-direction become high overwhelmingly, and the probability that multiple scattering occurs decreases extremely. Therefore, EXAFS vibration arises from interference of wave made by the electron which returns to atomic nucleus position after the single scattering by a neighboring atom. If the single scattering is assumed, the amplitude of this vibration can be obtained as a simple formula, which has a coordination number of the neighboring atom and an interatomic distance as parameters to the momentum k of the scattered electron. From a spectrum, it is possible to estimate the coordination number of the neighboring atom and the interatomic distance.

Measuring Method of XAFS

Measuring method of X-ray absorption spectroscopy includes general transmission method, fluorescence method (excitation-spectrum method) using fluorescence X-ray, electron yield method which monitors Auger electrons and secondary electrons relevant thereto, and the like. Since a hard X-ray having high transmittance is utilized for measurement of transition metals, rare earths, and the like, it is not necessary to set a measurement samples in a high vacuum, and it is possible to measure them under a gas atmosphere. Therefore in/situ measurement in a strict sense is possible. In addition, since X-ray absorption spectroscopy is a method for examining electronic transitions by X-ray absorption as mentioned above, it is unrelated to phase (solid, amorphous, liquid, gas) of the target sample.

The catalyst thus obtained is used for production of the alkylene oxide by partial oxidation of olefin in a vapor phase using a molecular oxygen-containing gas. As such olefin, ethylene, propylene, butene, butadiene and the like are included. Particularly, the catalyst is used for production of ethylene oxide from ethylene, and for production of 3,4-epoxybutene from 1,3-butadiene.

Here, as a molecular oxygen-containing gas, air, pure oxygen, a mixture of pure oxygen and an inert gas, oxygen enriched gas and the like are included.

For the oxidation reaction, well-known reactors which can be used for conventional vapor phase oxidation reaction of olefin can be used. Specifically, the total pressure of the supplying raw materials including olefin, the molecular oxygen-containing gas, and a diluted gas or a reaction regulation agent described below is 0.01 to 10 MPa, preferably 0.01 to 4 MPa, more preferably 0.02 to 3 MPa.

Into the reactor filled up with the catalyst of the present invention, in addition to a molecular oxygen-containing gas and olefin, one or two or more gas such as nitrogen, helium, argon, carbon dioxide and alkane can be mixed as a diluted gas and supplied together. The partial pressure of the gas needs to be such that it can be supplied into the reactor at the gas composition of outside an explosion limit.

A reaction regulator can also be blended in the raw material gas. As such a reaction regulator, a compound containing halogen is included, for example, chlorinated alkene with 1 to 6 carbons, such as chlorinated ethylene, vinyl chloride, methyl chloride, and t-butyl chloride, dichloromethane, dichloroethylene, trichloroethylene, chloroform, chlorinated benzene such as chlorinated biphenyl, monochlorobenzene, dichloropropane, dibromo propane, dichloropropene, dibromopropene, chrolobutane, bromobutane, dichlorobutane, dibromobutane, chlorobutene, brominated alkenes with 1 to 6 carbons, such as dibromoethylene, tribromoethylene, brominated ethylene, vinyl bromide, methyl bromide, t-butyl bromide, dibromomethane, tetrabromomethane, brominated benzene such as brominated biphenyl, monobrombenzene and the like can be exemplified, and one, or two or more of these can be used together. Among these, it is preferable to use vinyl chloride, or chlorinated ethylene. The concentration of the reaction regulator is 0.01 to 1000 ppm by volume, more preferably 0.1 to 100 ppm by volume, and especially 1 to 50 ppm by volume, based on the volume of the raw material gas.

As raw material gas composition, a mixed gas containing olefin of 0.5 to 40% by volume, preferably 10 to 30% by volume; oxygen of 3 to 10% by volume, preferably 6 to 9% by volume; carbon dioxide of 1 to 30% by volume, preferably 2 to 7% by volume; and the rest being an inert gas such as nitrogen, argon and steam, lower hydrocarbons such as methane and ethane, and further, the reaction regulator.

Although reaction temperature can be suitably selected according to the olefin to be used as the raw material, the reactor temperature at operation is 150 to 300° C., preferably 170 to 250° C.

The space velocity of the raw material gas to be supplied into the reactor is 100 to 30,000 hr$^{-1}$, more preferably 200 to 20,000 hr$^{-1}$, and further more preferably 1,000 to 10,000 hr$^{-1}$. In the reaction, conversion of 0.1 to 75% by mol, more preferably 1 to 60% by mol, and especially preferably 1 to 50% by mol of the olefin, the raw material, is enough and non-converted olefin may be re-circulated suitably into the reactor. That is, when supplying rate of the raw material is less than 100 hr$^{-1}$, production efficiency is lowered. On the other hand, when the supplying rate of the raw material is more than 30,000 hr$^-$, the conversion rate is lowered and it is not desirable. It should be noted that actual contact time required to achieve desired conversion level can be varied within a wide range depending on factors such as kinds or ratio to oxygen of the raw material gas to be supplied, supporting amount of the co-catalyst or the reaction promoter, supporting amount of the silver of the catalyst, quantity of the reaction regulator exists in the reaction gas, reaction temperature and reaction pressure.

Next, the present invention is explained in more detail using Examples and Comparative Examples.

It should be noted that, conversion rate and selectivity, which are described in Examples and Comparative Examples, are calculated by the following formulae.

(Formula 1)

Conversion rate (%)=((moles of ethylene reacted)/(moles of ethylene contained in the raw material gas))×100

(Formula 2)

Selectivity (%)=((moles of ethylene converted to ethylene oxide)/(moles of ethylene reacted))×100

EXAMPLE 1

95 parts by weight of alumina powder on the market (α-alumina having 1 to 2 μm of average primary particle size, 50 to 60 μm of average secondary particle size and 2.3 m$^2$/g of average BET specific surface area) and 10 parts by weight of organic binder (carboxymethyl cellulose) were put into a kneader, and sufficient mixed. Then, 4 parts by weight of alumina sol with the average particle size of 15 nm (as Al$_2$O$_3$ content), 1 part by weight of colloidal silica with the average particle size of 2 to 20 nm (as $SiO_2$ content) and apricot hull powder of 0.5 mm in average were added to the mixture, and 30 parts by weight of water was further charged into the kneader. After extrusion-molding the fully mixed alumina mixture, it was granulated to mean equivalent diameter of 8 mm, and dried at a temperature of 120° C. for 2 hours, and subsequently calcined at a temperature of 1500° C. for 2 hours. Subsequently, the carrier after being calcined was cooled down to 900° C. at a cooling rate of 10° C./min, and then it was cooled down to room temperature, to obtain carrier A. The obtained carrier was an α-alumina powder carrier having BET specific surface area of 2.0 m²/g, apparent porosity of 59%, pore volume of 39 cc/g, and water absorption rate of 39%.

Figure 2:
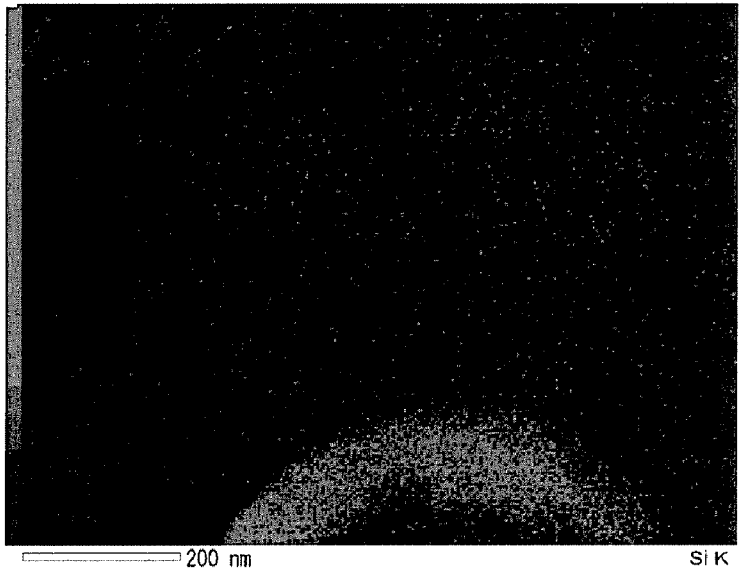
FIG. 2 is a photograph showing distribution of the silicon, for an identical part similarly, wherein white parts indicate silicon.
Figure 3:
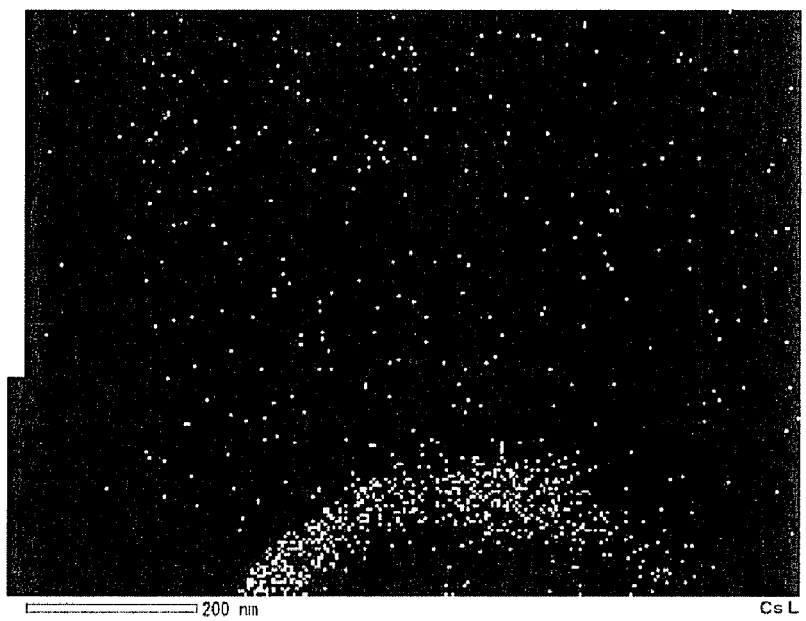
FIG. 3 is a photograph showing distribution of the cesium, for an identical part similarly, wherein white parts indicate cesium.

The carrier containing α-alumina as a main component thus obtained (54.4 g) was impregnated with a silver containing liquid consisting of 15 g of silver oxalate, 0.2 g of cesium nitrate, 8 ml of ethylenediamine and 12 g of water. Then, it was dried at 120° C. for 3 hours, to remove the liquid component. After heating this catalyst precursor supporting silver in an air flow preheated in advance at 250° C. for 30 minutes and heating in an air flow preheated in advance at 450° C. for 30 minutes, it was heated in a nitrogen flow preheated at 550° C. for 8 ours, to obtain catalyst (a). As to the catalyst (a), it was confirmed that Cs was localized on $SiO_2$ component of the carrier, from FE-TEM and EDS analysis, as shown in FIGS. 1 to 3.

The catalyst (a) was pulverized and sieved to be in the range between 600 and 850 meshes, and 1.2 g of the sieved catalyst was filled in the reaction tube made from the stainless steel having 3 mm of the inside diameter and 600 mm of tube length, and was subjected to vapor phase oxidization of ethylene under the following conditions. In the case where the conversion rate of ethylene is 10% relative to ethylene, the raw material, the selectivity of ethylene oxide after 120 hours was 82.2%, and the reaction temperature was 237° C.

<Reaction Conditions>
Space velocity: 5,500/hr
Reaction pressure: 2.1 MPa
Raw material gas: ethylene 20% by volume, oxygen 7.5% by volume, carbon dioxide 6% by volume, methane 50% by volume, argon 14% by volume, nitrogen 2.2% by volume, ethane 0.3% by volume, ethyl chloride 6 ppm by volume.

COMPARATIVE EXAMPLE 1

After the carrier having α-alumina as a main component (54.4 g, specific surface area: 2.2 m²/g, water absorption rate: 46%), was impregnated with a silver containing liquid consisting of 15 g of silver oxalate, 0.4 g of cesium nitrate, 8 ml of ethylenediamine and 12 g of water, it was dried at 120° C. for 3 hours to remove the liquid component. Catalyst (b) was obtained by heating this catalyst precursor supporting silver in an air flow at 280° C. for 48 hours.

As to the catalyst (b), it was confirmed that Cs was not localized on $SiO_2$ component of the carrier, from FE-TEM and EDS analysis, as shown in FIGS. 4 to 6. The catalyst (b) in which Cs is highly dispersed on the $SiO_2$ component of the carrier, was subjected to a reaction similar to that of Example 1. As a result, selectivity of ethylene oxide was 80.7%, and reaction temperature was 243° C.

INDUSTRIAL APPLICABILITY

The catalyst according to the present invention is useful for production of alkylene oxide by vapor phase oxidization of olefin with a molecular oxygen containing gas, particularly for production of ethylene oxide by oxidization of ethylene and for production of 3,4-epoxybutene by oxidization of 1,3-butadiene.

The invention claimed is:

1. A catalyst for partial oxidation of olefin which comprises silver or silver oxide and an alkali metal or a compound thereof supported on an α-alumina carrier containing silicon or a compound thereof, wherein the silicon or the compound thereof exists at a position substantially identical to that of a particle of the alkali metal or the compound thereof, wherein a localization frequency of the alkali metal or the compound thereof relative to the silicon or the compound thereof is 60% to 99.9%.

2. The catalyst according to claim 1, wherein a silver particle exists at a different position from that of (a) the silicon or the compound thereof and/or (b) the particle of the alkali metal or the compound thereof.

3. The catalyst according to claim 1, wherein content of (a) the silicon or the compound thereof, converted to as $SiO_2$, is 0.01 to 6% by mass relative to total amount of the carrier, and supported amount of (b) the alkali metal or the compound thereof (converted to as $M_2O$, wherein M is an alkali metal) and supported amount of (c) the silver are 0.01 to 5% by mass and 1 to 30% by mass, respectively, relative to α-alumina.

4. The catalyst according to claim 1, wherein content of (a) the silicon or the compound thereof, converted to as $SiO_2$, is 0.1 to 5% by mass relative to α-alumina, and supported amount of (b) the alkali metal or the compound thereof (converted to as $M_2O$, wherein M is an alkali metal) and supported amount (c) the silver are 0.01 to 5% by mass and 1 to 45% by mass, respectively, relative to α-alumina.

5. The catalyst according to claim 1, wherein content of α-alumina in the carrier is 89 to 99.9% by mass.

6. The catalyst according to claim 1, wherein the alkali metal is cesium.

7. A preparation method of the catalyst according to claim 1, wherein the method comprises impregnating an α-alumina carrier containing silicon or a compound thereof with an aqueous solution containing a silver compound and an alkali metal compound, drying the impregnated carrier, calcining the carrier in an oxidizing atmosphere at a temperature of 150 to 250° C. for 0.1 to 10 hours, further calcining the carrier in an oxidizing atmosphere at a temperature of 250 to 450° C. for 0.1 to 10 hours, and heat-treating the carrier in an inert gas atmosphere at a temperature of 450 to 700° C. for 0.1 to 10 hours.

8. The method according to claim 7, wherein α-alumina content in the carrier is 89 to 99.9% by mass and content of the silicon or the compound thereof, converted to as $SiO_2$, is 0.01 to 6% by mass.

9. A process for preparing olefin oxide which comprises subjecting olefin to vapor-phase oxidization with a molecular oxygen-containing gas in the presence of the catalyst set forth in claim 1.

10. The method according to claim 9, wherein the olefin is ethylene.

11. The catalyst according to claim 2, wherein content of (a) the silicon or the compound thereof, converted to as $SiO_2$, is 0.01 to 6% by mass relative to total amount of the carrier, and supported amount of (b) the alkali metal or the compound thereof (converted to as $M_2O$, wherein M is an alkali metal) and supported amount of (c) the silver are 0.01 to 5% by mass and 1 to 30% by mass, respectively, relative to α-alumina.

12. The catalyst according to claim 2, wherein content of (a) the silicon or the compound thereof, converted to as $SiO_2$, is 0.1 to 5% by mass relative to α-alumina, and supported amount of (b) the alkali metal or the compound thereof (converted to as M₂O, wherein M is an alkali metal) and supported amount (c) the silver are 0.01 to 5% by mass and 1 to 45% by mass, respectively, relative to α-alumina.

13. The catalyst according to claim 3, wherein content of (a) the silicon or the compound thereof, converted to as $SiO_2$, is 0.1 to 5% by mass relative to α-alumina, and supported amount of (b) the alkali metal or the compound thereof (converted to as $M_2O$, wherein M is an alkali metal) and supported amount (c) the silver are 0.01 to 5% by mass and 1 to 45% by mass, respectively, relative to α-alumina.

14. The catalyst according to claim 2, wherein content of α-alumina in the carrier is 89 to 99.9% by mass.

15. The catalyst according to claim 3, wherein content of α-alumina in the carrier is 89 to 99.9% by mass.

16. The catalyst according to claim 4, wherein content of α-alumina in the carrier is 89 to 99.9% by mass.

17. The catalyst according to claim 2, wherein the alkali metal is cesium.

18. The catalyst according to claim 3, wherein the alkali metal is cesium.

19. The catalyst according to claim 4, wherein the alkali metal is cesium.

20. The catalyst according to claim 5, wherein the alkali metal is cesium.

21. A process for preparing olefin oxide which comprises subjecting olefin to vapor-phase oxidization with a molecular oxygen-containing gas in the presence of the catalyst set forth in claim 2.

22. A process for preparing olefin oxide which comprises subjecting olefin to vapor-phase oxidization with a molecular oxygen-containing gas in the presence of the catalyst set forth in claim 3.

23. A process for preparing olefin oxide which comprises subjecting olefin to vapor-phase oxidization with a molecular oxygen-containing gas in the presence of the catalyst set forth in claim 4.

24. A process for preparing olefin oxide which comprises subjecting olefin to vapor-phase oxidization with a molecular oxygen-containing gas in the presence of the catalyst set forth in claim 5.

25. A process for preparing olefin oxide which comprises subjecting olefin to vapor-phase oxidization with a molecular oxygen-containing gas in the presence of the catalyst set forth in claim 6.

26. The catalyst according to claim 1, wherein the localization frequency of the alkali metal or the compound thereof relative to the silicon or the compound thereof is 80 to 99%.

* * * * *